United States Patent [19]
Wagner et al.

[11] Patent Number: 5,977,252
[45] Date of Patent: Nov. 2, 1999

[54] COVALENT MODIFICATION OF SURFACES WITH POLYMERS TO INCREASE BIOCOMPATIBILITY

[75] Inventors: William R. Wagner; Christopher R. Deible, both of Pittsburgh; Eric J. Beckman, Edgewood; Alan Russell, Wexford, all of Pa.

[73] Assignee: University of Pittsburgh, Pittsburgh, Pa.

[21] Appl. No.: 08/612,270

[22] Filed: Mar. 7, 1996

[51] Int. Cl.⁶ .......................... C08G 63/48; C08G 63/91; A01N 1/00
[52] U.S. Cl. ............................................. 525/54.1; 523/112
[58] Field of Search .............................. 525/54.1; 523/112

[56] References Cited

U.S. PATENT DOCUMENTS

| | | | |
|---|---|---|---|
| 4,046,722 | 9/1977 | Rowland | 525/54.1 |
| 4,373,009 | 2/1983 | Winn . | |
| 4,743,258 | 5/1988 | Ikada et al. . | |
| 5,462,990 | 10/1995 | Hubbell et al. . | |
| 5,580,923 | 12/1996 | Yeung et al. | 525/54.1 |

*Primary Examiner*—Nathan M. Nutter
*Attorney, Agent, or Firm*—Titus & McConomy

[57] ABSTRACT

Described herein is a technique for covalently modifying tissue and cellular surfaces to inhibit cell adhesion. The process described herein is conducted under conditions tolerable in vivo and employs a biocompatible polymer having a reactive group attached to at least one end that reacts with groups present or on tissue and cellular surfaces under aqueous and mild conditions and thereby covalently attaches the polymer to the tissue or cellular surface. Preferably, the reactive group attached to the polymer reacts with amines and hydroxyls present on tissue and cellular surfaces. In one preferred embodiment, the methods described herein provide for the covalent modification of tissue and cellular surfaces using a PEG-diisocyanate solution. The methods described herein are particularly useful in impairing platelet and leukocyte deposition in blood vessels and thereby thwarting thrombosis and restenosis, a common complication of vascular procedures including PTCA and vascular surgery. Furthermore, by masking the tissue surface proteins from blood elements, the methods described herein are useful in decreasing graft thrombogenicity and reducing the complications of vascular surgery. Finally the methods described herein reduce the immunogenicity of transplanted tissues and cells and thereby reduce the need for immunosuppressive therapy.

21 Claims, 11 Drawing Sheets

COVALENT MODIFICATION OF SURFACES WITH POLYMERS TO INCREASE BIOCOMPATIBILITY

FIELD OF THE INVENTION

The invention relates to modification of surfaces to increase biocompatibility and, in particular, to a technique for covalent modification of tissue and cellular surfaces using polymers.

BACKGROUND OF THE INVENTION

Researchers have employed a variety of techniques in an attempt to impair cell adhesion to a surface extant in a living organism or to be introduced into a living organism. Such techniques have significant medical applications because such techniques can be used to improve the biocompatibility of various procedures, transplants and implants. These techniques, however, have presented a variety of problems making their use in vivo, or for in vivo biologic transplants and implants, inappropriate. The technique described herein can be used in a variety of medical applications. In particular, the technique described herein has numerous applications for vascular procedures and biologic transplants. More specifically, the technique described herein, may be used to decrease blood vessel thrombosis and restenosis, reduce graft thrombosis, reduce the complications of vascular surgery and reduce the immunogenicity of transplanted tissues and cellular groups.

With respect to vascular procedures, researchers have sought to use a variety of methods to inhibit platelet deposition on damaged blood vessels because such deposition leads to thrombosis and restenosis. Restenosis primarily results from smooth muscle cell migration and mitosis in the inner layer of the blood vessel, a process known as intimal hyperplasia. When the luminal surface of a blood vessel is damaged, the subendothelial matrix proteins are exposed which triggers platelet deposition that can lead to acute vessel occlusion. Such damage may also trigger intimal hyper plasia through the release of platelet-derived factors. Platelet-released serotonin and thromboxane $A_2$ are vasoconstrictors currently thought to be important factors in acute vessel thrombotic occlusion. Platelet-derived growth factor ("PDGF") can stimulate smooth muscle cells to become mitoticaly active. Platelet granule release of PDGF, serotonin and leukotrienes, may also mediate migration of smooth muscle cells to the intimal layer of the vessel. Finally, proteases released from platelets, immune cells and cells damaged by mechanical trauma, may facilitate smooth muscle cell migration by breaking down physical boundaries such as the internal elastic lamina.

Such damage to blood vessels occurs during common vascular procedures such as percutaneous transluminal coronary angioplasty ("PTCA"). PTCA is an alternative to coronary artery bypass grafting, reopening blocked coronary arteries in patients with uncomplicated lesions in one or two vessels. PTCA has a high initial success rate although reocclusion caused by thrombosis and vasoconstriction currently occurs immediately after 2–4% of PTCA procedures. Furthermore, approximately 30–40% of arteries successfully opened by PTCA become reoccluded or restenosed, often within three months. PTCA is performed on more than 300,000 patients in the U.S. annually. Accordingly, modification of the PTCA technique by interrupting platelet deposition onto the injured intimal surface following PTCA, may provide substantial benefit in reducing intimal hyperplasia and coronary restenosis.

Blood vessels are similarly damaged during vascular surgery. Acute thrombotic occlusion at vascular anastomoses is a major complication of microvascular graft placement. Platelets respond to agonists and adhere to collagen and other adhesive proteins present at the anastomotic site resulting in platelet activation and further aggregation. Modification of the anastomotic site that results in a temporary non-thrombogenic coating would afford the anastomosis time to heal and eventually reendothelialize. Furthermore, temporary site specific masking of thrombogenic proteins may greatly reduce acute thrombosis and distal tissue ischemia without the use of systemic antiplatelet agents.

Vascular stent placement in conjunction with coronary angioplasty has grown in popularity as a technique to improve long term vessel patency. Such stents work by providing the vessel with support against mechanical recoil. Stent placement does not inhibit platelet deposition and platelet-mediated hyperplasia and reocclusion by intimal hyperplasia remains a common occurrence with stent placement. Furthermore, the advantages offered by a stent can be offset by increased vascular complications stemming from the stent such as damage to the arterial wall, improper stent openings, and bleeding and dissection at the access site. These complications generally result in longer hospital stays. Accordingly, a technique that permitted development of a coating might be used in lieu of stent placement, or as an adjuvant to stent placement, i.e., one that permitted retention of the significant mechanical benefits of the stent while reducing acute thrombosis and hyperplasia, would be a significant benefit.

A variety of techniques have been employed to inhibit platelet deposition, including systemic delivery of pharmaceuticals. Unfortunately, systemic delivery of pharmaceuticals is associated with an increased risk for bleeding complications.

Investigators also have attempted to inhibit platelet deposition using polymer gels. At least theoretically, because these gels degrade by scission, they create an added risk for embolism during the degradation process. Several in the field have attempted to inhibit platelet deposition and have reported greatly reduced thrombosis on damaged arterial sections coated with a polyethylene glycol ("PEG") gel polymerized with photoactivation and initiators. For example, a technique reported by Hubbell et al. (U.S Pat. No. 5,468,505 to Hubbell et al.) uses light activated eosin Y ("EY") and triethanolamine ("TEA") to initiate polymerization of PEG-diacrylate on vessel surfaces to inhibit surface platelet deposition. Unfortunately, these methods often require numerous steps to accomplish the modification.

The prior art also includes descriptions of covalent modification of suspended proteins with functionalized polyethylene glycol. Unfortunately, the parameters for temperature, pH, time and toxic factors/byproducts for such methodologies are inconsistent with their use with biological tissues.

Others in the field are investigating a variety of genetic engineering strategies to preclude vascular restenosis. Unfortunately, the genetic engineering approaches present significant regulatory and technical hurdles. Genetic transformation often requires exposure of the vessel to viral vectors and may be accompanied by poorly controlled cellular transformation. Furthermore, genetic transformation may induce inflammation, be more expensive, and act less quickly to prevent platelet deposition than the technique described herein.

Researchers have also sought a way to decrease temporarily the immunogenicity of transplanted tissues and cells.

Current techniques for immunoisolating transplanted cells (e.g. encapsulation) remain problematic. A modification of a transplanted surface that would decrease the immunogenicity of transplanted cells and tissues would reduce the need for immunosuppressive therapy. Similarly, a surface modification technique might also be used to protect cells on microcarriers in blood or plasma contacting bioreactors. An example of such an application involves the bioartificial liver in which researchers currently use immunoisolative membranes or encapsulation to isolate cells. Transplantation researchers have sought a way to induce host tolerance for transplanted grafts. A technique that masks the immunogenic antigens of the transplanted materials until the host can establish tolerance for cell transplants and whole organ transplants would be a useful conjugate to other methodologies designed to induce tolerance in transplant recipients. Furthermore, a technique that reduces acute thrombosis, fibrinolysis, and complements activation in a donor organ would provide significant clinical benefit.

Thus, a need still exists in the art for an economical and efficient method for modifying tissue and cellular surfaces, under conditions tolerable in vivo, such that they exhibit cell adhesion impairing characteristics. In particular, a need still exists in the art for a method for impairing platelet and leukocyte deposition on vessel surfaces, under conditions tolerable in vivo, following vascular surgery or trauma.

The following abbreviations are used by Applicants throughout the application:

ANOVA=analysis of variance
ECGM=endothelial cell growth media with endothelial growth factors
EDTA=ethylene diaminetetra-acetic acid
EY=eosin Y
HCAEC=human coronary arterial endothelial cells
HT=Hepes-Tyrodes mixture
MW=molecular weight
PEG=polyethylene glycol
PTCA=percutaneous transluminal coronary angioplasty
TEA=triethanolamine

SUMMARY OF THE INVENTION

The invention described herein is based on the principle that reactive groups on cellular and tissue surfaces can be modified by covalently attaching a water-soluble polymer through a reactive group attached to at least one end of the polymer. Preferably, the reactive end group of the polymer will react with the amine and hydroxyl groups present on a tissue or cellular surface and thereby covalently modify that surface. Any biocompatible polymer can be used. A group that can react, under mild aqueous conditions, with groups present on tissue and cellular surfaces, including amines and hydroxyls, is attached to at least one end of the polymer. The characteristics of the reactive end group determine how quickly the covalent modification is achieved.

Unlike the prior art, the technique described herein permits, under conditions compatible with in vivo procedures, covalent polymer modification of the surface so that the polymer is attached directly to the surface tissue proteins or surface cellular proteins to mask adhesive or antigenic ligands. Furthermore, in contrast to the prior art technique that uses light, polymer coupling to amine and possibly hydroxyl groups on the tissue or cellular surface occurs rapidly enough at near physiologic conditions to make a high degree of protein modification possible without the use of light or photoinitiators.

When used in vascular procedures, the invention is based on the principle that factors released from platelets and possibly leukocytes depositing on a damaged vascular wall, prompt smooth muscle cell growth and chemotaxis. By masking thrombogenic vascular wall proteins from blood cell interactions with covalently attached polymers, the inventive technique inhibits initial platelet and leukocyte deposition and eliminates the prompting event for mitotic activation and chemotaxis. The polymer used in the procedure reacts directly with amine and hydroxyl residues on surface tissue proteins and covalently attaches the polymer to these proteins under conditions tolerable in vivo. Thus, when used in vascular procedures such as PTCA, direct covalent modification of the vascular lumen with a polymer should reduce the incidence of coronary restenosis after PTCA.

The technique described herein has several advantages over techniques currently being developed or employed. For example, greater efficacy with polymer surface modification is achieved because the thrombogenic nidus is locally masked while patient platelet function is preserved. See FIGS. 1*a* and 1*b*. The polymer surface modification technique also has an advantage economically and theoretically over proposed techniques to locally deliver monoclonal antibodies or bioactive peptides to mask specific adhesive ligands. Monoclonal antibodies are expensive to produce and difficult to obtain while polymers are readily available and relatively inexpensive. Furthermore, monoclonal antibodies are limited by and specific to the antigens present on the tissue or cellular surface, while a polymer can attach to a variety of loci on the surfaces.

With respect to photopolymerizable arterial gel coating used by other investigators, the technique described herein is superior for a variety of reasons. For example, the polymer covalent modification strategy described herein does not require a light source or photoinitiators associated with the photopolymerizable gel technique. Furthermore, because the technique described herein provides for direct attachment of the polymer to surface proteins, the polymer is removed slowly as the vessel naturally remodels. The gel described in the prior art relies upon scission of biodegradable linkages within the polymer for gel breakdown. The degradation process for a photopolymerizable gel and the technique described herein are illustrated in FIGS. 2*a* and 2*b* respectively. Thus, the technique described herein appears to have a lower likelihood of generating potentially damaging emboli in the healing process.

Distinctions between the photopolymerizable gel technique's effect and operation on vessels and the technique described herein are readily apparent through a comparison of a scanning electron micrograph of a human placental artery coated with a photopolymerized gel (See FIG. 3) and a human placental artery coated using the technique described herein (See FIG. 6*b*). The gel creates a homogenous surface while the technique described herein maintains the integrity of the vessel contours and permits better evaluation of the underlying vessel.

Covalent modification of surfaces with a polymer also is well suited to be used in lieu of or as an adjuvant to placing a stent in vessels. If used as an adjuvant, it may be possible to retain the significant mechanical benefits of the stent while reducing acute thrombosis and hyperplasia.

Furthermore, the reaction kinetics of the described technique suggest that the modification can be achieved with a reaction time below one minute. Those skilled in the art will appreciate that typically modification of proteins requires hours and days. When the technique described herein is applied to blood vessels, the fast reaction and lack of photoinitiation requirements will minimize vessel ischemia times and the complexity of the delivery modality, including a catheter, thereby reducing the risk of complications.

Finally, the technique described herein does not require the genetic modification of human cells. Accordingly, unlike the genetic engineering strategies being investigated, polymer surface modification poses fewer regulatory and technical hurdles and is less likely to induce inflammation, less expensive, and acts immediately to prevent platelet deposition.

In sum, the covalent modification of surfaces described herein offers many advantages over the prior art. For example, when applied in vascular procedures, the technique described herein offers many advantages over current and proposed techniques. It exhibits fast kinetics, provides broad ligand coverage localized to the site of vessel damage, and is amenable to relatively simple delivery strategies. No permanent intravascular device, with its attendant complications, is required for technique described herein. Polymer covalent modification will also degrade safely as the vessel naturally remodels and heals. Furthermore, the byproducts of such degradation are non-toxic.

An object of the invention is to provide a technique for covalent modification of tissue or cellular surfaces under conditions that are tolerable in vivo.

Another object of the invention is to reduce complications in a variety of intravascular procedures and following vascular trauma.

A further object of the invention is to reduce the incidence of restenosis following vascular procedures, including PTCA, that either use or do not use intravascular stent placement.

Another object of the invention is to increase the initial success rates of vascular procedures, including PTCA, by preventing acute reocclusion caused by thrombosis and vasoconstriction.

A further object of the invention is to provide a technique for improving the biocompatibility of transplanted cells and tissues by preventing platelet, leukocyte and bacterial adhesions.

Other advantages of the invention will be apparent from a perusal of the following detailed description of a presently preferred embodiment taken in connection with the accompanying drawings.

DETAILED DESCRIPTION OF THE INVENTION

Disclosed herein is a method for covalently modifying tissue and cellular surfaces to increase biocompatibility. The invention described herein is based on the principle that reactive groups on cellular and tissue surfaces can be modified by covalently attaching a water-soluble polymer through a reactive group attached to the end of the polymer. Any water-soluble polymer can be used provided it is of sufficient length such that when a multitude of the polymers are attached covalently to the surface and they assume their natural formation, the polymer multitude creates a barrier that substantially covers the tissue or cellular surface to be modified. Thus, for example, polypeptides and saccharides can be used as the polymer. Preferably, the polymer PEG is used because of its demonstrated high biocompatibility.

Any group that can covalently react, under mild aqueous conditions, with reactive groups present on tissue and cellular surfaces, including amines and hydroxyls, can be attached to at least one end of the polymer. The characteristics of the reactive end group determine how quickly the covalent modification is achieved. Because tissue surfaces and in vivo cellular surfaces typically present a large number of amine and hydroxyl groups, the reactive end group attached to the polymer preferably will react with the amine and hydroxyl groups present on the tissue or cellular surface, and thereby covalently modify that surface and attach the polymer. To react with the amine and hydroxyl groups present on tissue and cellular surfaces, the reactive end group attached to the polymer can be an ester, anhydride (including N-carboxy anhydride), isocyanate aldehyde, tosylate, tresylate or epoxide. Reactive end groups that will not release small molecules or toxic molecules upon the covalent attachment of the polymer are preferred. Consequently, cyclo-esters, cyclo-anhydrides and isocyanates are preferred reactive groups to attach to the end of the polymer and effectuate the covalent modification. In particular, diisocyanate is preferred because its reaction time with amine and hydroxyl groups on tissue and cellular surfaces has been demonstrated to be less than a minute. To react with molecular groups other than amine and hydroxyl groups present on tissue and cellular surfaces, malemide may also be used in the technique described herein.

The technique described herein can be applied to a tissue or cellular implant prior to its implantation to improve the biocompatibility of the implant. When used in vivo, a solution containing a polymer with one of the reactive end groups can be applied at the desired site using whatever methodology is appropriate with the locus of the desired cite (e.g. injection or catheter). The fast kinetics of the covalent modification generally ensures that the technique will operate only in the desired locus. Mechanical barriers, such as those created by certain catheters, may also be erected to ensure that the covalent modification is limited to the desired area.

The Applicants present evidentiary material herein that demonstrate the characteristics of surfaces treated with a polymer capable of covalent attachment and the methods of the present invention. The invention will be further understood by the following non-limiting examples and preferred embodiments.

EXAMPLE ONE

PEG-diisocyanate Modification of Vessel Surfaces

To validate the protocol used herein and the methods for detecting platelet deposition, Applicants replicated the techniques to impair platelet deposition posed by other inventors and were able to achieve similar results. Photopolymerizable PEG gels were impregnated onto damaged arterial segments to assess their effect on platelet deposition in the system described above. The photopolymerized gels used in the experiments described herein were created by methods described by Hubbell et al. except 400 MW and 1000 MW PEG-diacrylate were used instead of 18,500 MW PEG-tetraacrylate. Vessel surfaces were incubated in 4% EY for 1 minute then washed with Hepes-Tyrodes (HT) buffer at pH 7.4. A solution of 0.5 ml of 23% PEG-diacrylate (MW400) and 5 $\mu$l of mixture of 10 ml 3.5% TEA and 200 $\mu$l n-vinylpyrrolidinone was applied to the surface drop by drop until the vessel was covered with a light coat and exposed to ultraviolet light (10 watts/cm$^2$) for 5 minutes to maximize polymer gelation. The gels were washed with HT buffer at pH 7.4 to remove unpolymerized PEG. FIG. 4 depicts results from 7 experiments, each bar representing the mean of up to four vessels tested. Both 400 MW and 1000 MW PEG-diacrylate gels demonstrated a significant reduction in platelet deposition (p<0.05), and were not significantly different from each other (p>0.5).

To demonstrate the technique described herein, a PEG-diisocyanate solution was created by dissolving 0.2 grams PEG (MW3400)-diisocyanate (Shearwater Polymers, Huntsville, Ala.) in one ml of phosphate buffered saline adjusted to pH 8.0. The polymer PEG was chosen for its hydrophilicity, water solubility and demonstrated biocompatability. Diisocyanate was chosen because of its particularly fast reaction time with amine and hydroxyl groups. Arterial segments from human placentas were modified by immersing the luminal surface of the segments with the PEG-diisocyanate solution for 30, 15, 5 and 1 minute(s). To examine the effect of physically adsorbed PEG and establish the critical nature of the functional end group, vessel segments were also incubated with PEG lacking an end group capable of covalently reacting with proteins on the vessel surface. The control was created using 0.2 grams PEG (MW3400) (non-reactive) dissolved in 1 ml phosphate buffered saline at pH 8.0, and the vessels were incubated for periods of 30 and 1 minute(s).

To evaluate the effectiveness of various PEG vessel coatings and modifications, experiments were performed flowing whole human blood with $^{111}$indium labeled platelets over damaged arteries coated with PEG in a perfusion system previously described by Badimon et al. in *J. Lab. Clin. Med.*, 1987, 110(6):750-12. The model used for coronary arteries following PTCA was the deendothelialized human placental artery. Placentas obtained within two hours of delivery were rinsed and the chorionic membrane was removed. These placental arteries were isolated whole and cut longitudinally through branch points to minimize leaking and were scraped with a metal spatula to remove the endothelium. Blood for perfusion was obtained from the antecubital vein of healthy volunteers who had been aspirin free for 10 days, i.e. they were non-anticoagulated. The blood was labeled with $^{111}$indium oxine (Mallhlrodt, St. Louis, Mo.) as previously described by Johnson et al. in Plast. Reconst. Surg., 1992, 90(4):650-8.A., and reconstituted with red blood cells and plasma just before perfusion.

As shown in FIG. 5, platelet deposition on vessels covalently modified with PEG-diisocyanate for a reaction time of 30 minutes was significantly reduced compared to control, non-treated vessels and vessels treated with non-reactive PEG, termed PEG adsorbed (p<0.0005). Vessels exposed to and covalently modified with PEG-diisocyanate reacted for 5 and 15 minutes also exhibited significantly lower platelet deposition than PEG adsorbed segments (p<0.05). These results indicate the effectiveness and suitability of polymers in preventing cellular interactions when the tissue or cellular surface is modified by the covalent attachment of that polymer. More particularly, these results indicate the effectiveness and suitability of covalently attached PEG in preventing cellular interactions when reacted with a tissue surface. Platelet deposition on vessel segments reacted for 5 minutes or 15 minutes did not vary significantly from those of 30 minutes (p>0.9). Because of variation in platelet activity, results of the 30, 15 and 5 minute immersions are expressed as a ratio of platelet deposition on PEG-diisocyanate treated vessels divided by deposition on untreated denuded vessels exposed to platelets for 30 minutes. Results for vessels immersed in PEG-diisocyanate solution for 1 minute are expressed as a ratio of platelet deposition on PEG-diisocyanate treated vessels divided by deposition on untreated denuded vessels exposed to platelets for 1 minute. For all tests, an analysis of variance ("ANOVA") was used to determine if there was a statistical difference present between test groups, and p values between groups were obtained using the Neuman-Keuls test.

The efficacy of the technique was readily apparent when scanning electron micrographs of the treated and untreated vessels were compared. FIG. 6a depicts a scanning electron micrograph of an untreated denuded placental artery subjected to the protocol described above. Many platelets can be observed attached to the tissue surface. The attachment and spreading of the platelets to the tissue surface reflect the high surface thrombogenicity of the untreated denuded placental artery. In contrast, FIG. 6b depicts a scanning electron micrograph of a denuded placental artery treated using the technique described herein, and more specifically with a solution of PEG-diisocyanate as described above. Very few platelets are attached to the treated vessel and those platelets that are attached do not exhibit any spread thereby indicating the low thrombogenicity of the treated vessel. Finally, FIG. 6c depicts a scanning electron micrograph of a denuded placental artery treated with a polymer lacking a reactive group that permits it to covalently attach to the tissue surface. In the present example, a solution of PEG-OH was applied to the denuded placental artery following the same protocol used to treat the placental artery with PEG-diisocyanate. As with the untreated denuded placental artery, many platelets are attached to and spreading on the tissue surface thereby indicating high surface thrombogenicity.

EXAMPLE TWO

Photopolymerizable PEG Gel-Treated Grafts

To farther demonstrate the efficacy of the technique described herein and to validate the testing methods use to evaluate the technique described herein, Applicants applied the technique to preclotted Dacron. The surface of preclotted Dacron Medox, Oakland, N.J.) was covalently modified with PEG-diisocyanate using the same reaction conditions as above. Photopolymerized gels also were coated onto Dacron grafts using PEG-diacrylate (MW 400). As shown in FIG. 7, both PEG-diisocyanate modified grafts and photopolymerizable gel treated grafts, modified using the technique described above to validate the testing methods of the experiments used herein, exhibited significantly lower platelet deposition (p<0.05) than untreated preclotted dacron vascular grafts.

EXAMPLE 3

Toxicity Data Demonstrating Biocompatability of the Present Invention with Human Coronary Arterial Endothelial Cells The following describes preferred methods of culturing human coronary arterial endothelial cells used to demonstrate the present invention. In the experiments reflected herein, commercially grown and cryo-stored cultured human coronary arterial endothelial cells ("HCAEC") were obtained from Clonetics. The endothelial cells were seeded in 75 cm$^2$ culture flasks and the subsequent populations were divided to create numerous homogenous subcultures. ECGM was added to the cultures to maintain them. ECGM was removed from the flask and approximately 1 ml of trypsin with 0.25% or EDTA (weight/volume) was added to remove any residual ECGM. Approximately 5 to 7 ml of trypsin with 0.25% EDTA (weight/volume) was added and maintained at 37° for approximately ten minutes to allow removal of the cells from the culture flask surface. To ensure that all the cells were removed, the cultures were submitted to a visual microscopic inspection.

After the endothelial cells were detached from the flask surface, they were suspended in Media 199 (Sigma) such that the total volume of the suspension fluid and cellular matter comprised 50 cc. The conical tube was place in a centrifuge and spun for six minutes at 1100 rpm to permit separation of the endothelial cells from the media. After the separation process was accomplished through centrifugation, the media was removed from the conical tube using a pipet.

An endothelial cell growth media containing endothelial growth factors ("ECGM") (provided by Clonetics) was added to each conical tube containing a cellular pellet. ECGM was added to resuspend the cellular pellet. After resuspension of the cellular pellet, the endothelial cell population was divided into individual wells to create homogenous subcultures. Sufficient ECGM was added to each endothelial cell subculture so that on visual inspection all the cells were covered with a thin layer of ECGM. To ensure efficient cell growth, ECGM was replaced every two to three days as indicated by manufacturers' instructions.

Three treatment groups were established: (1) the "direct group" in which a PEG-diisocyanate solution was applied directly to HCAEC; (2) the "media group" in which ECGM was added to HCAEC and a PEG-diisocyanate solution was subsequently added; and (3) the "control group" in which no PEG-diisocyanate solution was added. In both the direct and media groups, a PEG-diisocyanate solution was used made using 0.2 g PEG-diisocyanate per ml of phosphate buffered saline (pH 8.0). In the direct group, the ECGM covering the HCAEC was removed using a pipet and the PEG-diisocyanate solution was added directly to the HCAEC drop by drop until all the HCAEC appeared covered upon visual inspection. After the HCAEC/PEG-diisocyanate mixture was incubated for one minute, ECGM was added. In the media group, an amount of the PEG-diisocyanate solution equal to that used in each subculture of the direct group, was added directly to the HCAEC in ECGM, i.e., ECGM was not removed before the PEG-diisocyanate solution was added. In the control group, ECGM was removed from the wells containing HCAEC, the wells were incubated for one minute, and ECGM was added to the HCAEC.

The PEG-diisocyanate solution was added to subcultures of the direct and media groups at varying times to determine the effect of the PEG-diisocyanate solution immediately after cell adhesion, during rapid cell growth and at cellular confluency, as confirmed by visual inspection. Accordingly, the PEG-diisocyanate solution was added to subcultures of the direct and media groups at the following intervals after subculture creation: (1) two to four hours (i.e., immediately after cell adhesion); (2) one to two days (i.e., during rapid growth); and (3) four to seven days (i.e., during confluency). A population count was computed using a sampling method.

The results of these experiments are presented in FIG. 8. The normalized growth ratio of the HCAEC (expressed as the number of cells on day 0, 2 and 6 divided by the number of cells on day 0) following exposure to PEG-diisocyanate at days 0 and 2, are presented in FIG. 8. The data show the PEG-diisocyanate solution had a modest effect on the HCAEC by decreasing cell growth immediately following treatment. However, the HCAEC treated with the PEG-diisocyanate solution recovered to become confluent within a day of when the control cells became confluent.

Similarly, FIG. 9 reflects the average growth ratio of the HCAEC (expressed as the number of cells on days 2, 6 and 9 divided by the number of cells on day 0) following exposure to PEG-diisocyanate at day 0. FIG. 9 also reflects standard deviation bars for the experiments depicted therein. Again, there is no significant difference in the growth rate between the treatment groups. When the PEG-diisocyanate solution was added to confluent HCAEC of the direct and media groups, no effect was observed on the morphology or cell population vis-a-vis the control group.

EXAMPLE 4

Toxicity Data Demonstrating Biocompatibility of the Present Invention with Human Fibroblast Cells To further demonstrate the biocompatibility of the technique described herein, fibroblasts were isolated from samples of human skin tissue and grown up. The human fibroblasts were immersed in a solution of PEG-diisocyanate according to the protocol used for the direct described above. The growth of the fibroblast cells was measured four days following such exposure to a PEG-diisocyanate solution made using the technique described in example 1 above. The results of these experiments are presented in FIG. 10. The results show that the technique described herein, and more particularly, the technique described herein using a PEG-diisocyanate solution, had no effect on the growth of the human fibroblast cells.

Figure 1A:
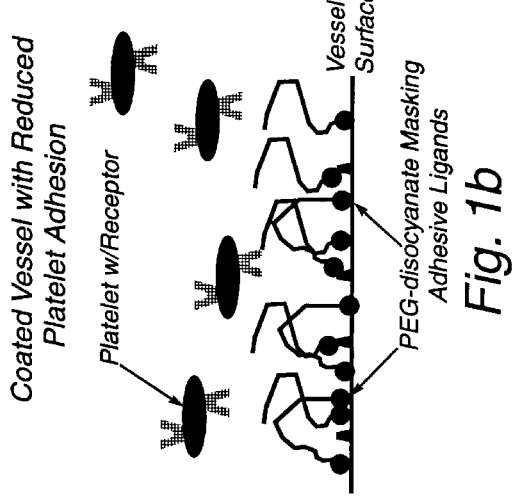
FIG. 1a is a schematic representation of an untreated tissue surface showing the attachment mechanism of platelets to that surface.
Figure 1B:
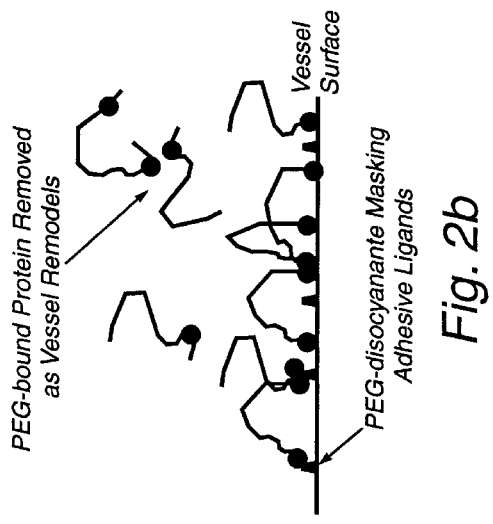
FIG. 1b is a schematic representation of covalently modified vessel in which the adhesive ligands have been masked to reduce cellular adhesion.
Figure 2A:
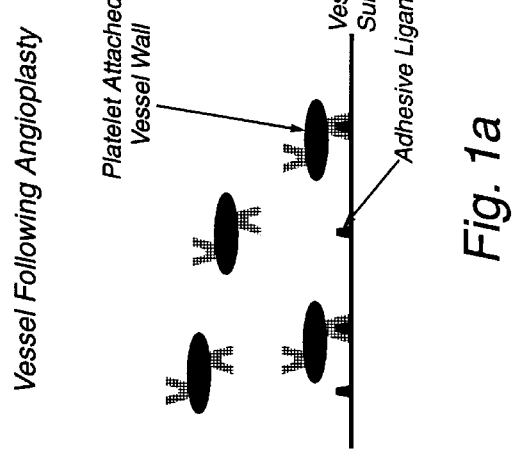
FIG. 2a is a schematic representation of the degradation process of a gel attached to a biological surface.
Figure 2B:
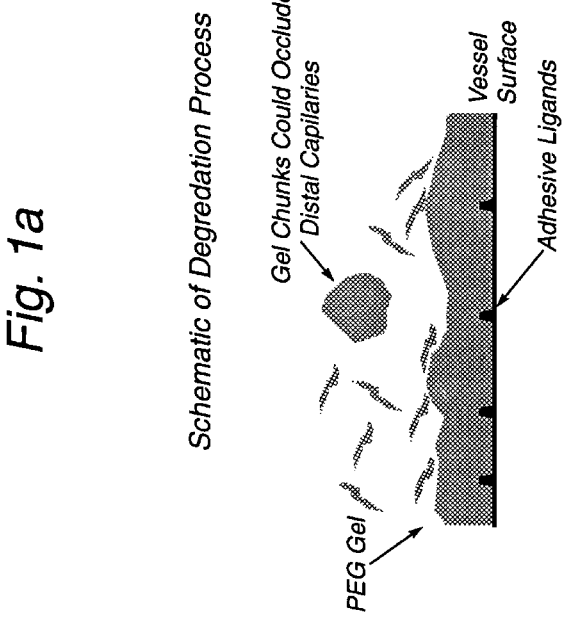
FIG. 2b is a schematic representation of the degradation process of a tissue surface covalently modified using the technique described herein.
Figure 3:
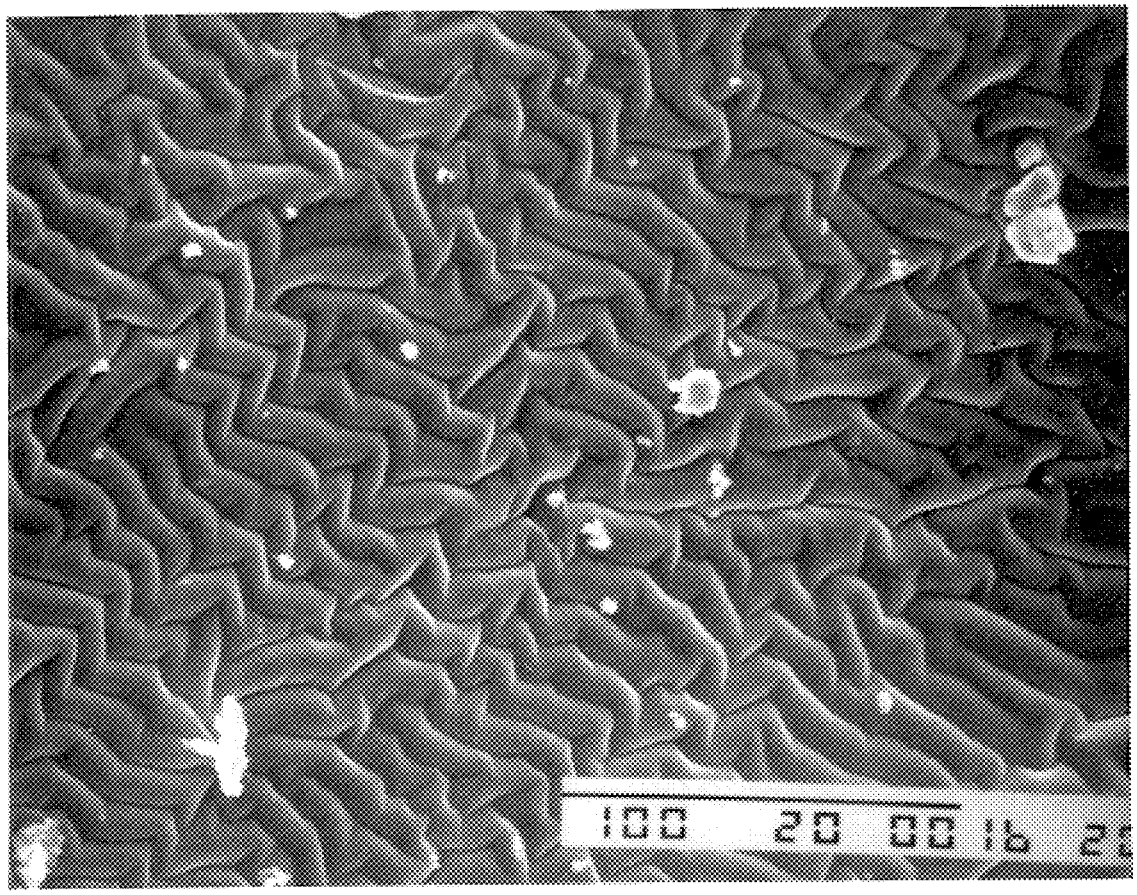
FIG. 3 is an illustrative scanning electron micrograph of a placental artery coated with a photopolymerized gel, wherein the scale bar represents 10 microns.
Figure 4:
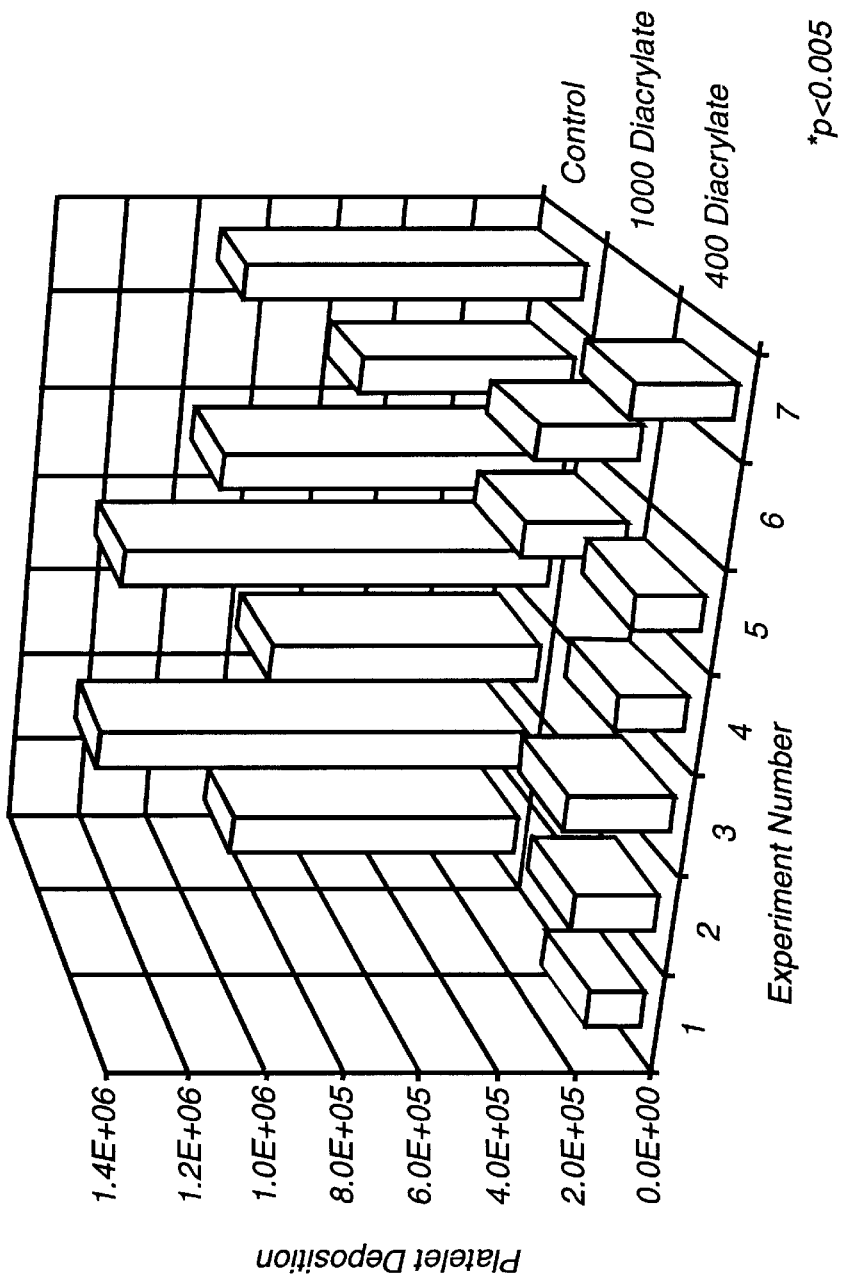
FIG. 4 reflects results of 7 experiments and the daily averages of $^{111}$Indium-labeled platelet deposition on photopolymerizable PEG gel coated arteries, wherein each bar represents the mean of up to four arteries tested.
Figure 5:
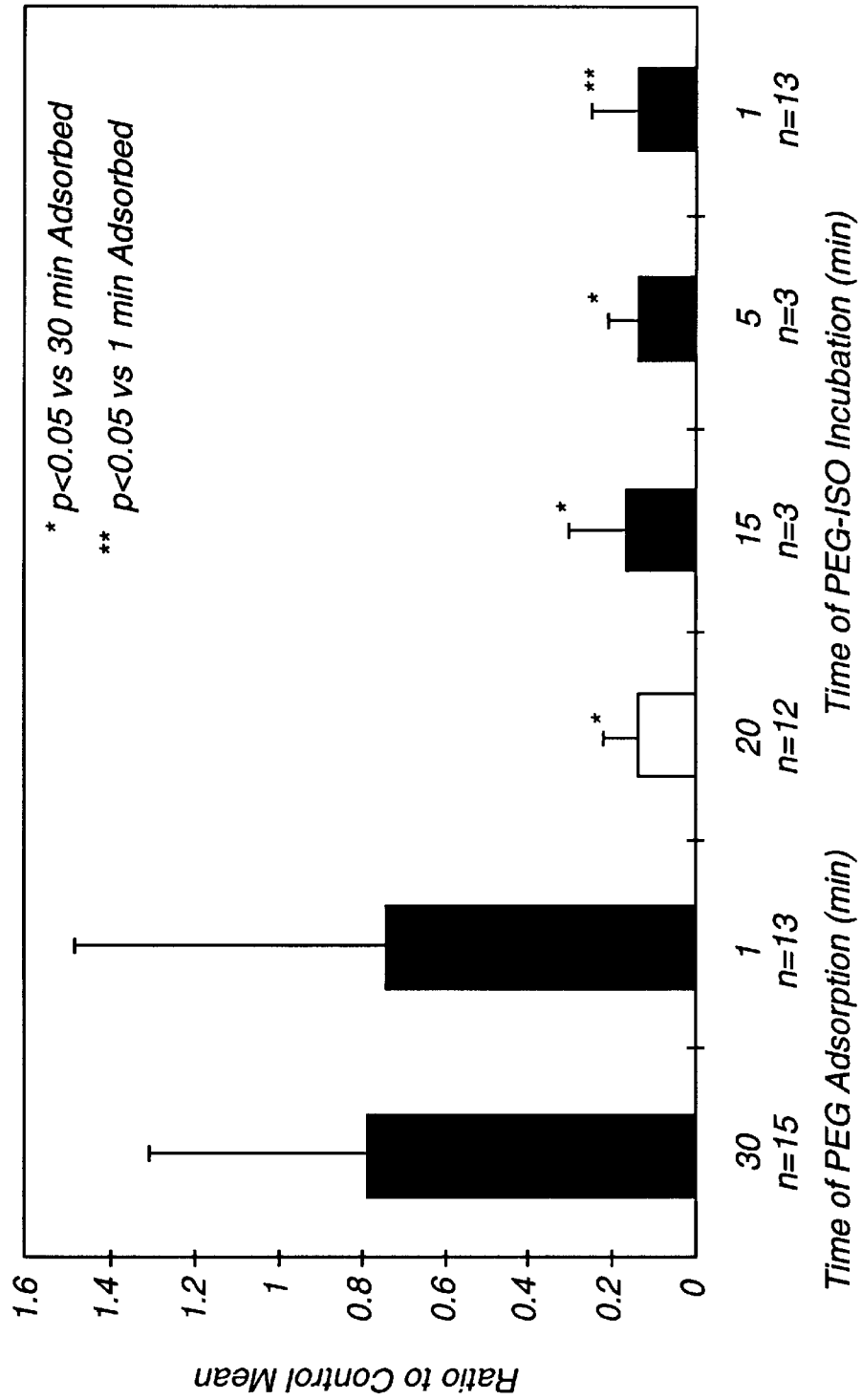
FIG. 5 reflects the results of experiments, expressed as the ratio of $^{111}$Indium-labeled platelet deposition on PEG-diisocyanate modified arterial surfaces to daily control mean, in which human placental arteries were exposed to PEG-diisocyanate for 30, 15, 5 and 1 minute(s).
Figure 6A:
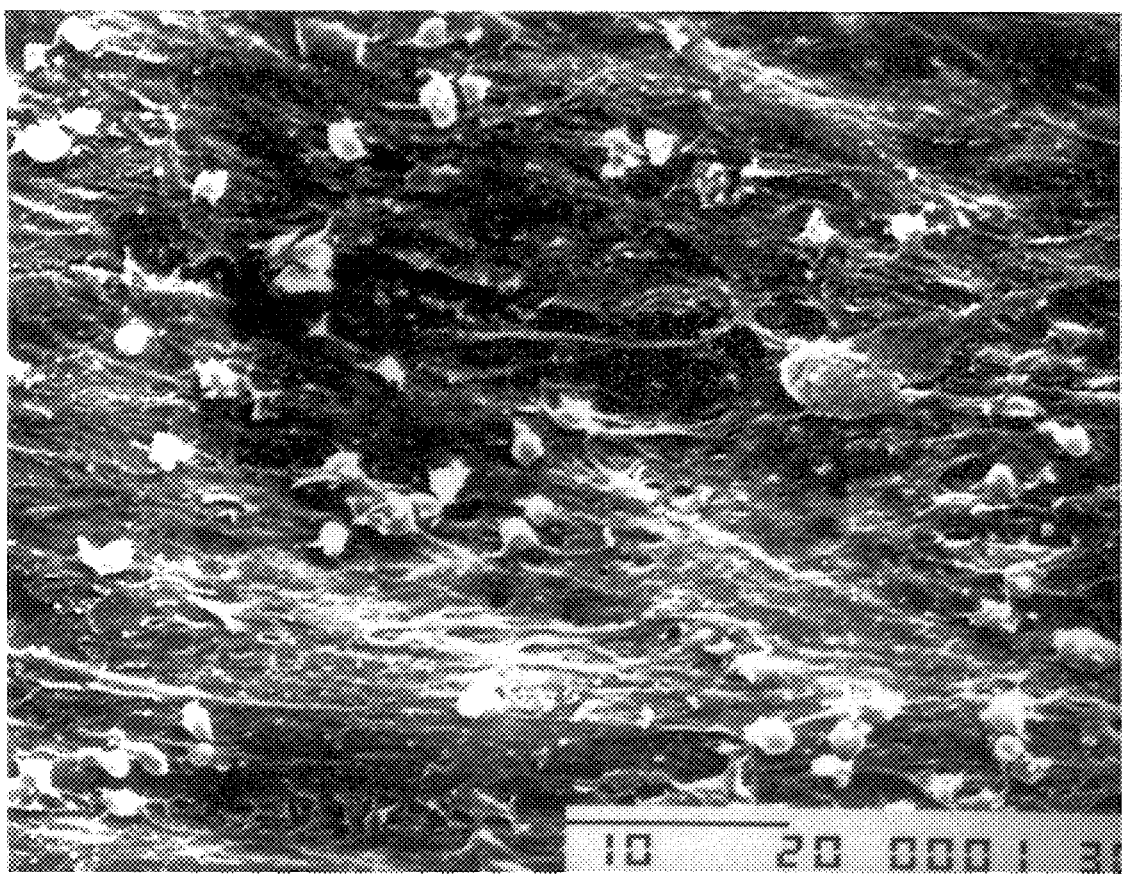
FIG. 6a depicts a scanning electron micrograph of an untreated denuded placental artery, wherein the scale bar represents 10 microns.
Figure 6B:
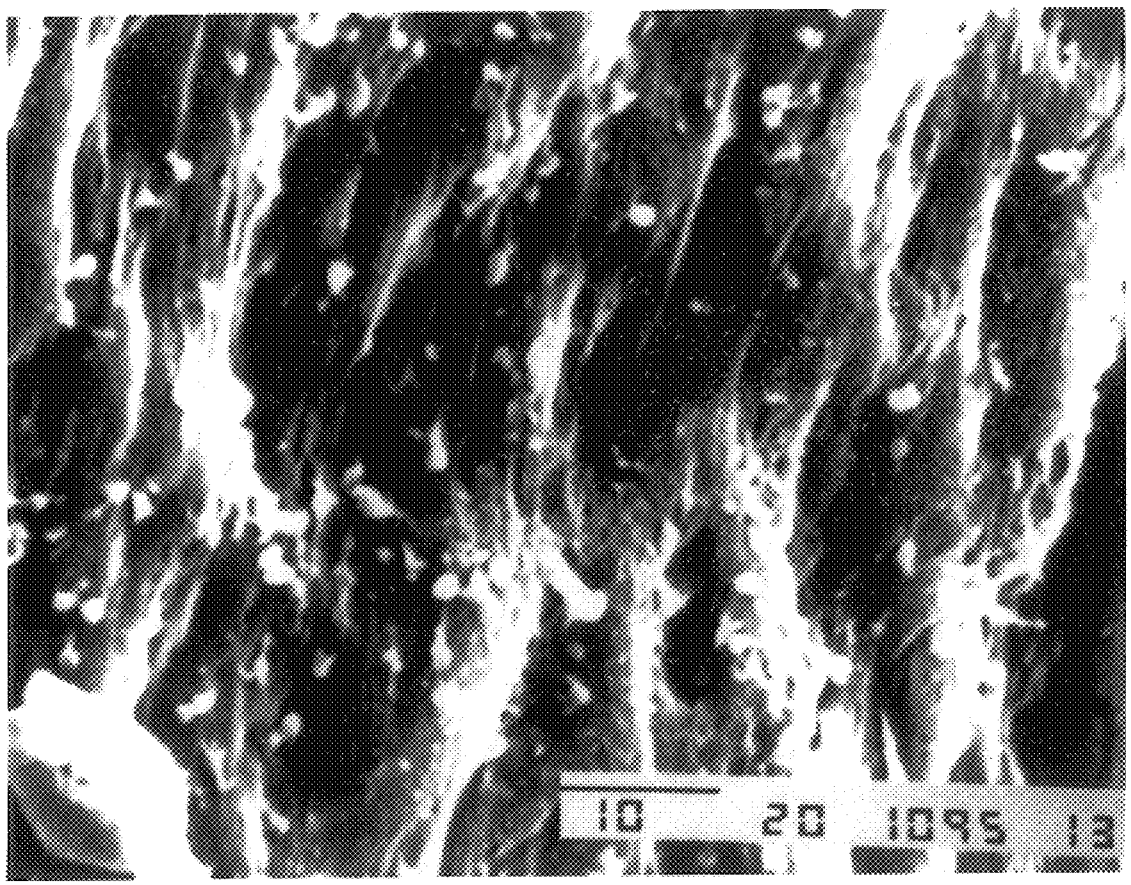
FIG. 6b depicts a scanning electron micrograph of a denuded placental artery covalently modified using a solution of PEG-diisocyante, wherein the scale bar represents 10 microns.
Figure 6C:
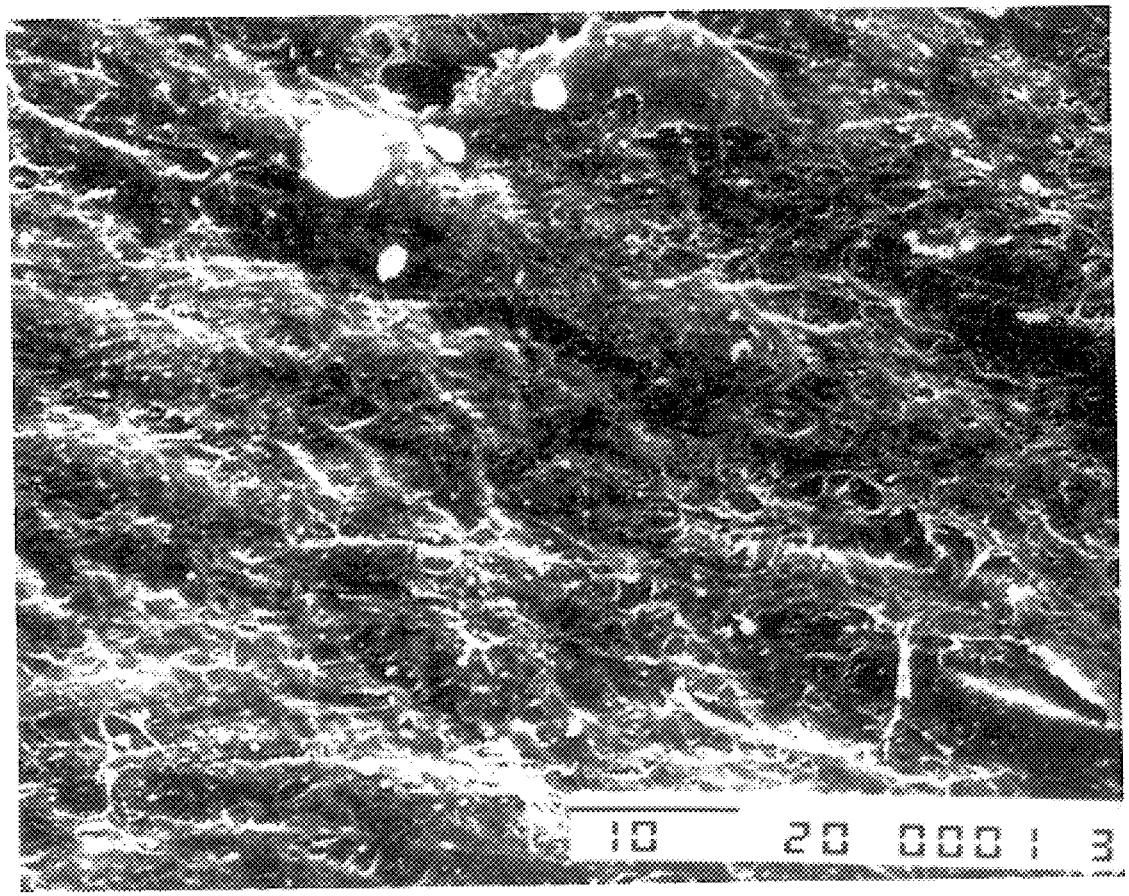
FIG. 6c depicts a scanning electron micrograph of a denuded placental artery treated with a polymer that lacks a reactive group that permits it to covalently attach to the tissue surface, wherein the scale bar represents 10 microns.
Figure 7:
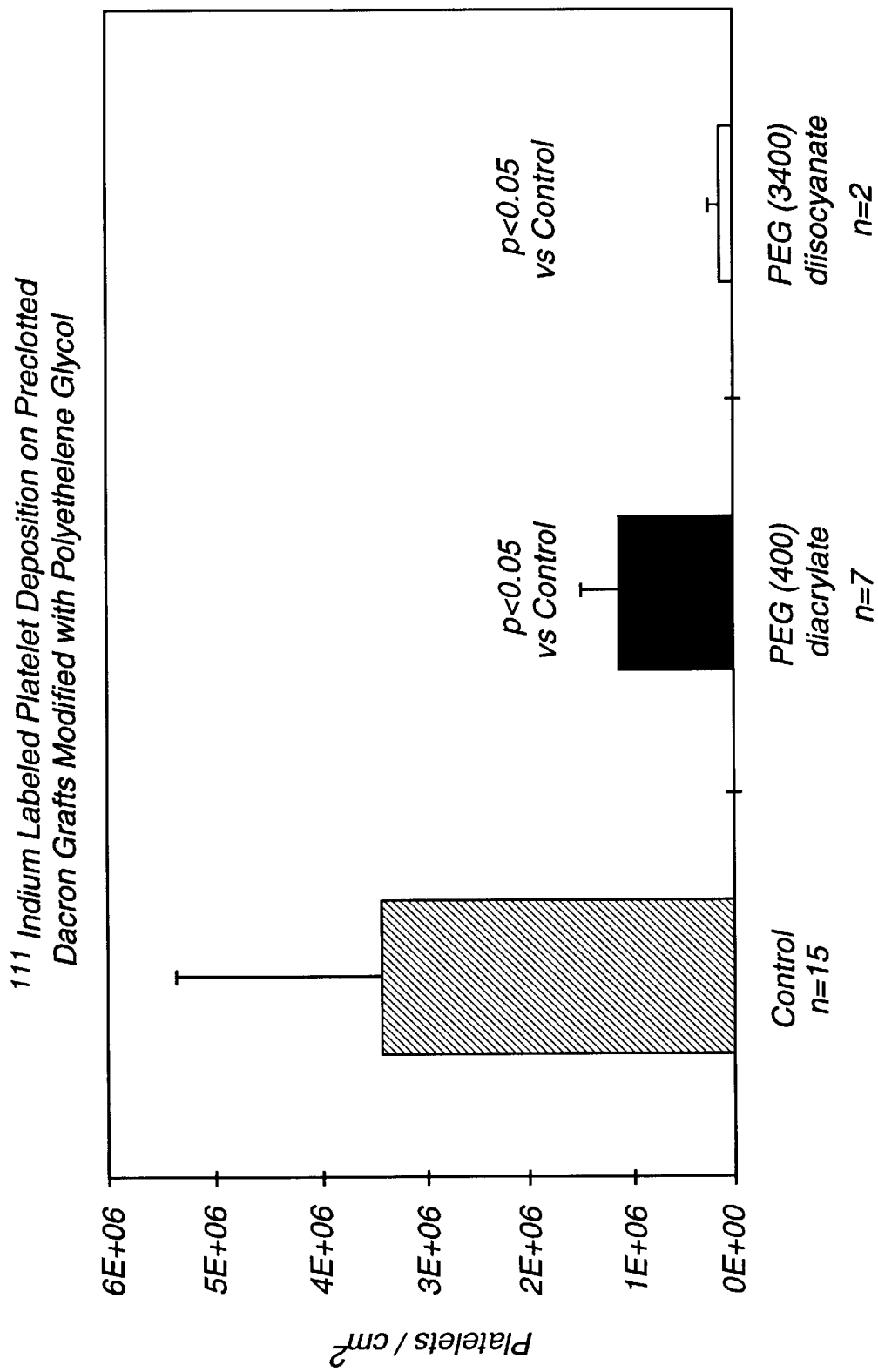
FIG. 7 reflects $^{111}$Indium-labeled platelet deposition on preclotted dacron grafts modified with polyethylene glycol and platelet deposition on untreated preclotted dacron grafts.
Figure 8:
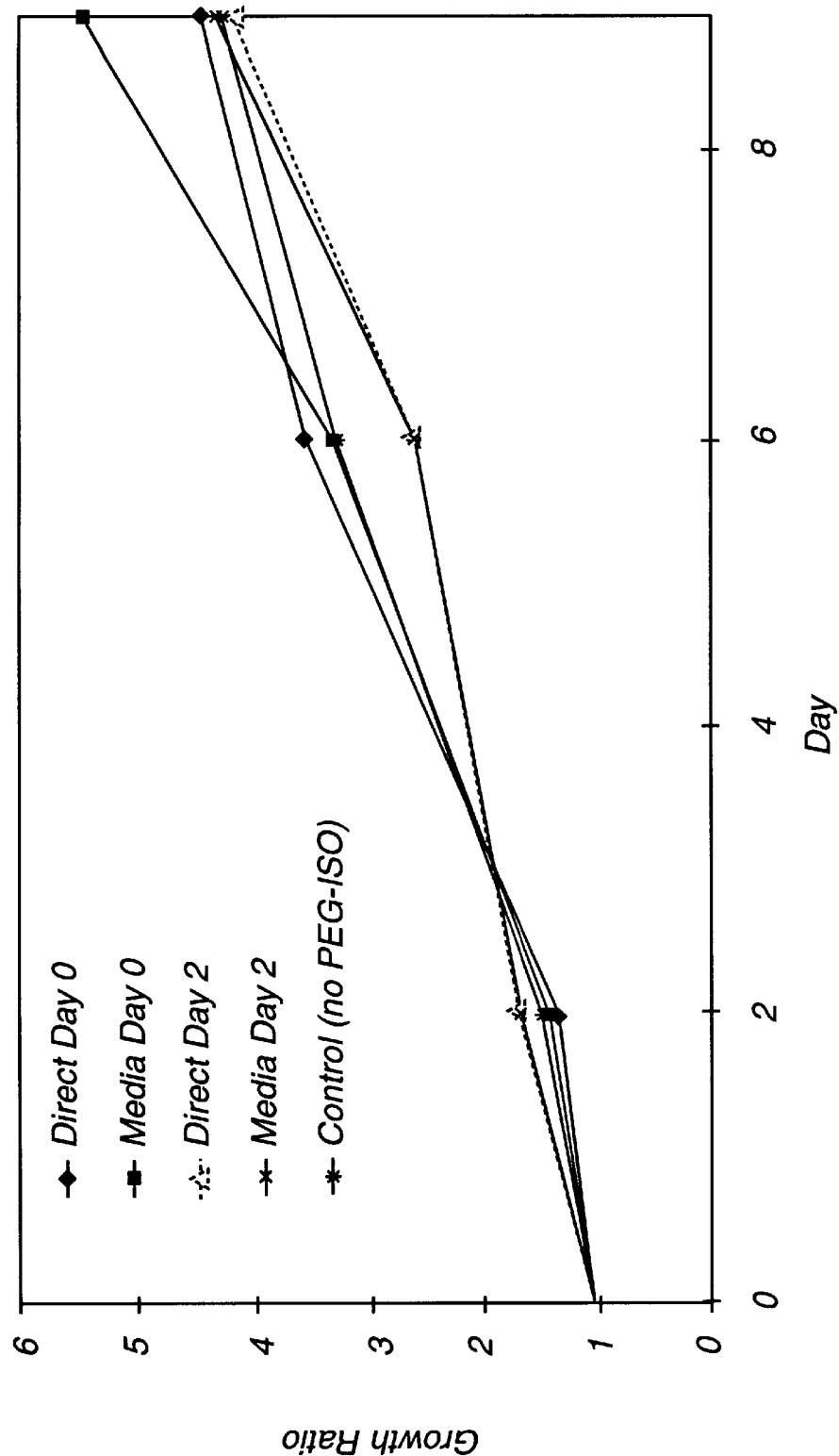
FIG. 8 depicts the plotted results of toxicity experiments in which PEG-diisocyanate was applied to HCAEC at days 0 and 2, wherein the normalize growth ratio of the HCAEC (expressed as the number of cells on day 0, 2 and 6 divided by the number of cells on day 0) is presented for experiments in which PEG-diisocyanate was applied directly to the HCAEC (shown as "direct" groups), applied to HCAEC in growth media (shown as "media" groups), or not applied (shown as the "control" group).
Figure 9:
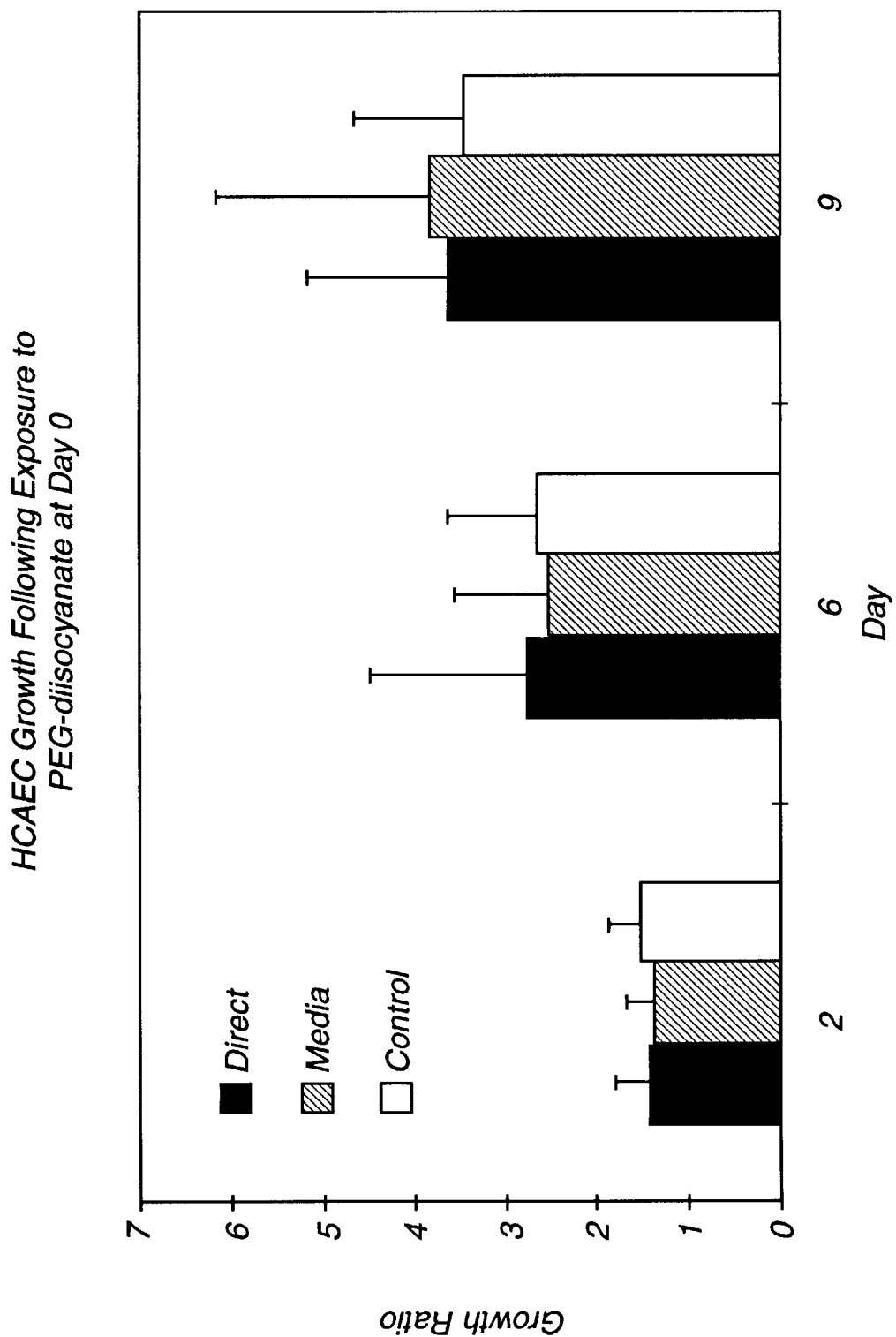
FIG. 9 depicts a bar graph reflecting the results of toxicity experiments of PEG-diisocyanate applications to HCAEC, wherein the average growth ratio of HCAEC (growth ration is expressed as the number of cells on day 2, 6 and 9, divided by the number of cells on day 0) following exposure to PEG-diisocyante at day 0, and wherein the PEG-diisocyanate was applied directly to the HCAEC (shown as "direct" groups), applied to HCAEC in growth media (shown as "media" groups), or not at all (shown as the "control" group), and wherein standard deviation error bars are shown.
Figure 10:
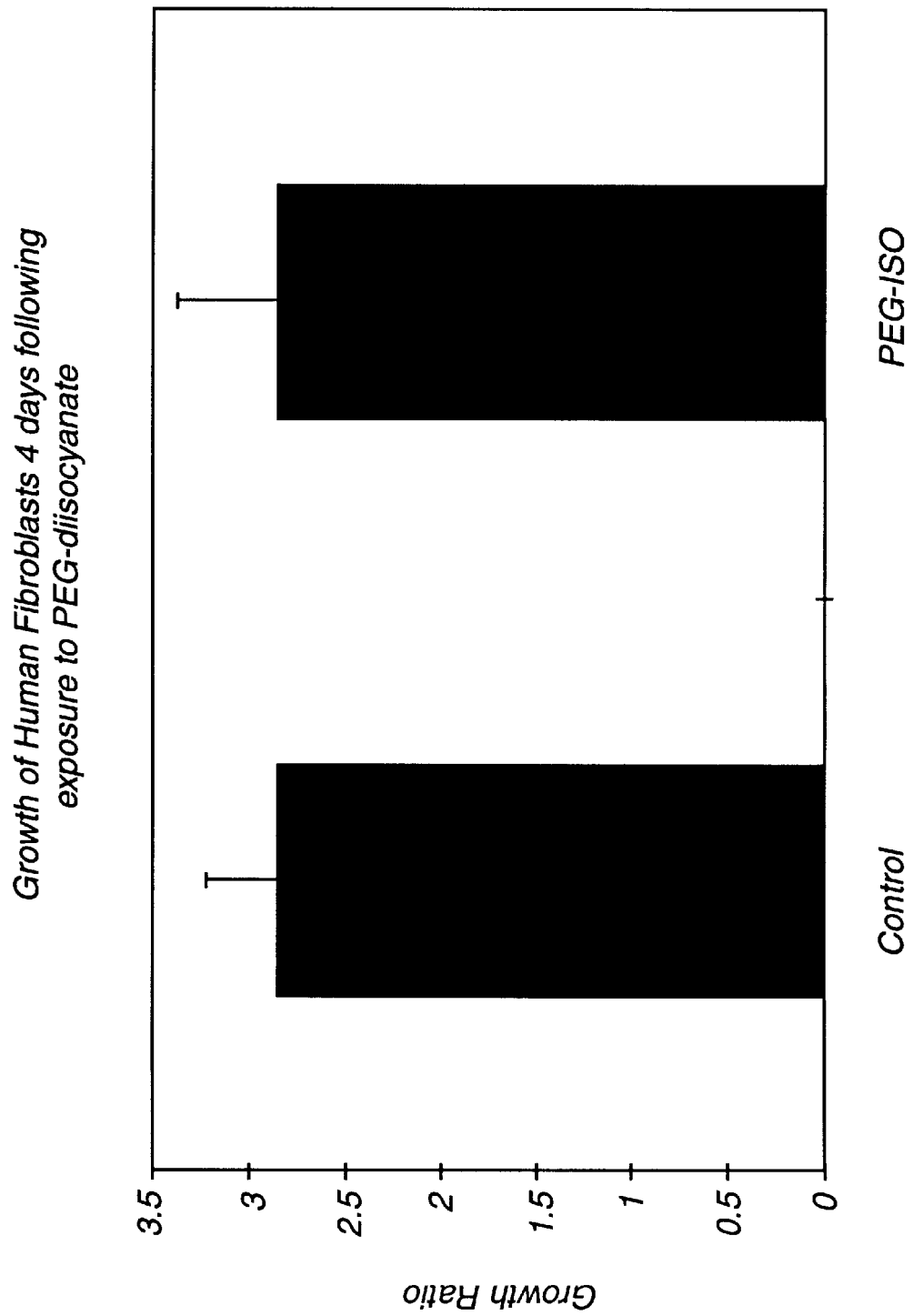
FIG. 10 is a graph depicting the growth of human fibroblast cells 4 days following exposure to a PEG-diisocyanate solution and the growth of untreated human fibroblast cells after 4 days (control).

What is claimed:

1. A method of covalent modification of tissue and cellular surfaces with polymers comprising covalent coupling of a biocompatible polymer having at least one end functional group that reacts, under conditions tolerable in vivo, with groups present on tissue and cellular surfaces.

2. A method of covalent modification of tissue and cellular surfaces with polymers comprising covalent coupling of a biocompatible polymer having at least one end functional group that reacts, under conditions tolerable in vivo, with groups present on tissue and cellular surfaces, wherein the tissue or cellular surface is exposed to a solution containing the biocompatible polymer with at least one functional end group.

3. A method of covalent modification of tissue and cellular surfaces with polymers comprising covalent coupling of a biocompatible polymer having at least one functional end group that reacts, under conditions tolerable in vivo, with amine and hydroxyl groups on tissue and cellular surfaces.

4. A method of covalent modification of tissue and cellular surfaces with polymers comprising covalent coupling of a biocompatible polymer having at least one functional end group that reacts, under conditions tolerable in vivo, with amine and hydroxyl groups on tissue and cellular surfaces and wherein the tissue or cellular surface is exposed to a solution containing the biocompatible polymer with at least one functional end group.

5. A method for impairing cell adhesion to tissue or cellular surfaces comprising covalent coupling of a biocompatible polymer having at least one functionalized end group that reacts, under conditions tolerable in vivo, with amine and hydroxyl groups on tissue or cellular surfaces.

6. A method for selectively impairing platelet and leukocyte adhesion to tissue or cellular surfaces comprising covalent coupling of a biocompatible polymer having at least one functionalized end group that reacts, under conditions tolerable in vivo, with amine and hydroxyl groups on tissue or cellular surfaces.

7. A method of modifying vascular tissue surfaces comprising covalently attaching, under conditions tolerable in vivo, a biocompatible polymer having at least one functional end group that reacts with the amine and hydroxyl groups on the vascular tissue surface.

8. A method of reducing thrombosis and restenosis of blood vessels after vascular procedures or injury comprising covalently attaching, under conditions tolerable in vivo, a biocompatible polymer having at least one functional end group that reacts with the amine and hydroxyl groups on the blood vessel tissue surface.

9. A method of improving percutaneous coronary transluminal angioplasty comprising covalently attaching, under conditions tolerable in vivo, a biocompatible polymer having at least one functional end group that reacts with the amine and hydroxyl groups on blood vessel tissue surface.

10. A method of reducing the immunogenicity of tissue or cellular transplants comprising covalent modification of tissue and cellular transplant surfaces with polymers wherein a biocompatible polymer having at least one end functional group, is covalently coupled, under conditions tolerable in vivo, with groups present on tissue and cellular surfaces.

11. The method of claims 1 or 2, wherein the functional end group is an ester, anhydride, isocyanate, aldehyde, tosylate, tresylate, epoxide or maleimide.

12. The method of any of claims 1 through 10, wherein the functional end group is an ester, anhydride, isocyanate, aldehyde, tosylate, tresylate or epoxide.

13. The method of any of claims 1 through 10, wherein the functional end group is a cyclo-ester, cyclo-anhydride or isocyanate.

14. The method of any of claims 1 through 10, wherein the biocompatible polymer has diisocyanate attached as functional end groups.

15. The method of any of claims 1 through 10, wherein the biocompatible polymer is polyethylene glycol.

16. The method of any of claims 1 through 10, wherein the biocompatible polymer is polyethylene glycol and the functional end group is an ester, anhydride, isocyanate, aldehyde, tosylate, tresylate, epoxide or maleimide.

17. The method of any of claims 1 through 10, wherein the biocompatible polymer is polyethylene glycol and the functional end group is a cyclo-ester, cyclo-anhydride or isocyanate.

18. The method of any of claims 1 through 10, wherein the polymer is polyethylene glycol and the functional end group is diisocyanate.

19. The method of any of claims 1 through 10, wherein the tissue or cellular surface is exposed to a solution containing polyethylene glycol(MW3400)-diisocyanate in phosphate buffered saline.

20. The method of any of claims 1 through 10, wherein the tissue or cellular surface is exposed to a solution containing polyethylene glycol(3400)-diisocyanate in phosphate buffered saline and the pH of the solution is adjusted to pH 8.0.

21. A method of covalent modification of tissue and cellular surfaces with polymers comprising covalent coupling of a biocompatible polymer having at least one end functional group that reacts, under conditions compatible with maintaining cellular viability, with groups present on tissue and cellular surfaces.

* * * * *